United States Patent
Daley et al.

(10) Patent No.: US 6,723,892 B1
(45) Date of Patent: Apr. 20, 2004

(54) PERSONAL CARE PRODUCTS HAVING REDUCED LEAKAGE

(75) Inventors: Michael Allen Daley, Alpharetta, GA (US); Bruce Wilfuhr Achter, Alpharetta, GA (US); Charles Wilson Colman, Marietta, GA (US); Joseph DiPalma, Neenah, WI (US); David Martin Jackson, Roswell, GA (US); Nancy Donaldson Kollin, Roswell, GA (US); Margaret Gwyn Latimer, Alpharetta, GA (US); Gregory Marc Lefkowitz, Atlanta, GA (US); Sylvia Bandy Little, Marietta, GA (US); David Michael Matela, Alpharetta, GA (US); David Charles Potts, Dunwoody, GA (US); Lawrence Howell Sawyer, Neenah, WI (US); Kristin Ann Goerg-Wood, Sherwood, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/653,389

(22) Filed: Sep. 1, 2000

Related U.S. Application Data

(60) Provisional application No. 60/159,352, filed on Oct. 14, 1999.

(51) Int. Cl.[7] .................................................. A61F 13/15
(52) U.S. Cl. ....................................................... 604/378
(58) Field of Search ............................ 604/378, 385.01

(56) References Cited

U.S. PATENT DOCUMENTS

| | | | |
|---|---|---|---|
| 2,357,392 A | 9/1944 | Francis, Jr. ................... | 18/47.5 |
| 3,121,427 A | 2/1964 | Mosier ........................ | 128/284 |
| 3,710,793 A | 1/1973 | Glassman ..................... | 128/285 |
| 3,730,184 A | 5/1973 | Mesek ......................... | 128/287 |
| 3,765,418 A | 10/1973 | Jones, Sr. .................... | 128/287 |
| 3,855,046 A | 12/1974 | Hansen et al. ............... | 161/150 |
| 3,881,488 A | 5/1975 | Delanty et al. .............. | 128/287 |
| 3,888,257 A | 6/1975 | Cook et al. .................. | 128/296 |
| 3,934,588 A | 1/1976 | Mesek et al. ........... | 128/290 W |

(List continued on next page.)

FOREIGN PATENT DOCUMENTS

| | | | |
|---|---|---|---|
| EP | 0 202 472 | 11/1986 | ........... D21H/5/26 |
| EP | 0 483 730 | 5/1992 | ........... A61F/13/15 |
| EP | 0 494 112 | 7/1992 | ........... A61F/13/15 |
| EP | 0 518 291 | 12/1992 | ........... A61F/13/15 |
| EP | 0 523 683 | 1/1993 | ........... A61F/13/46 |

(List continued on next page.)

OTHER PUBLICATIONS

Chatterjee's Absorbency, Elsevier Science Publishers, B.V. 1985, pp. 36–40.
Article by R.W. Hoyland and R. Field in the journal *Paper Technology and Industry*, Dec. 1976, p. 291–299.

Primary Examiner—Weilun Lo
(74) Attorney, Agent, or Firm—James B. Robinson; Steven D. Flack

(57) ABSTRACT

There is provided an absorbent system that not only takes in fluid, but then transfers that fluid further beneath the first composite. This is achieved in this invention through paired permeability, capillarity, and void volume of the first and second composites. The invention is an absorbent system composed of at least two absorbent composites that have complementary structural/surface energy characteristics. Such an absorbent system has a first absorbent Composite A which has a first permeability, a first capillarity, and a first void volume and at least one second absorbent Composite B which has a second capillarity and a second porosity multiplied by second thickness. The first absorbent Composite A is in liquid communication or contact with at least one second absorbent Composite B, such that the first absorbent Composite A, and the second absorbent Composite B have a fluid partitioning amount in Composite A, a third triple intake time (IT3) and a rewet value.

9 Claims, 3 Drawing Sheets

U.S. PATENT DOCUMENTS

| | | | | |
|---|---|---|---|---|
| 3,993,820 A | 11/1976 | Repke | ............ | 428/167 |
| 4,079,739 A | 3/1978 | Whitehead | ............ | 128/290 R |
| 4,100,324 A | 7/1978 | Anderson et al. | ............ | 428/288 |
| 4,212,302 A | 7/1980 | Karami | ............ | 128/287 |
| 4,213,459 A | 7/1980 | Sigl et al. | ............ | 128/287 |
| 4,223,677 A | 9/1980 | Anderson | ............ | 128/287 |
| 4,333,463 A | 6/1982 | Holtman | ............ | 128/287 |
| 4,340,563 A | 7/1982 | Appel et al. | ............ | 264/518 |
| 4,341,217 A | 7/1982 | Ferguson et al. | ............ | 128/290 W |
| 4,375,448 A | 3/1983 | Appel et al. | ............ | 264/518 |
| 4,383,376 A | 5/1983 | Numamoto et al. | ............ | 34/9 |
| 4,392,908 A | 7/1983 | Dehnel | ............ | 427/194 |
| 4,449,979 A | 5/1984 | Holtman | ............ | 604/379 |
| 4,494,278 A | 1/1985 | Kroyer et al. | ............ | 19/304 |
| 4,560,372 A | 12/1985 | Pieniak | ............ | 604/369 |
| 4,585,448 A | 4/1986 | Enloe | ............ | 604/378 |
| 4,600,462 A | 7/1986 | Watt | ............ | 156/278 |
| 4,639,254 A | 1/1987 | LeGault et al. | ............ | 604/385 R |
| 4,640,810 A | 2/1987 | Laursen et al. | ............ | 264/518 |
| 4,668,566 A | 5/1987 | Braun | ............ | 428/286 |
| 4,670,011 A | 6/1987 | Mesek | ............ | 604/378 |
| 4,675,209 A | 6/1987 | Pedigrew | ............ | 427/194 |
| 4,685,915 A | 8/1987 | Hasse et al. | ............ | 604/378 |
| 4,699,619 A | 10/1987 | Bernardin | ............ | 604/378 |
| 4,701,177 A | 10/1987 | Ellis et al. | ............ | 604/385 A |
| 4,773,903 A | 9/1988 | Weisman et al. | ............ | 604/368 |
| 4,795,453 A | 1/1989 | Wolfe | ............ | 604/385.1 |
| 4,865,596 A | 9/1989 | Weisman et al. | ............ | 604/368 |
| 4,908,026 A | 3/1990 | Sukiennik et al. | ............ | 604/378 |
| 4,923,454 A | 5/1990 | Seymour et al. | ............ | 604/368 |
| 4,950,264 A | 8/1990 | Osborn, III | ............ | 604/385.1 |
| 4,960,477 A | 10/1990 | Mesek | ............ | 156/209 |
| 4,973,325 A | 11/1990 | Sherrod et al. | ............ | 604/368 |
| 4,994,037 A | 2/1991 | Bernardin | ............ | 604/368 |
| 5,009,650 A | 4/1991 | Bernardin | ............ | 604/368 |
| 5,030,229 A | 7/1991 | Yang | ............ | 604/385.1 |
| 5,079,074 A | 1/1992 | Steagall et al. | ............ | 428/218 |
| 5,087,506 A | 2/1992 | Palumbo | ............ | 428/194 |
| 5,092,860 A | 3/1992 | Pigneul | ............ | 604/380 |
| 5,104,396 A | 4/1992 | Oatley et al. | ............ | 604/379 |
| 5,171,302 A | 12/1992 | Buell | ............ | 604/385.1 |
| 5,176,668 A | 1/1993 | Bernardin | ............ | 604/368 |
| 5,197,959 A | 3/1993 | Buell | ............ | 604/385.1 |
| 5,248,309 A | 9/1993 | Serbiak et al. | ............ | 604/368 |
| 5,252,374 A | 10/1993 | Larsonneur | ............ | 428/77 |
| 5,277,976 A | 1/1994 | Hogle et al. | ............ | 428/397 |
| 5,294,478 A | 3/1994 | Wanek et al. | ............ | 428/218 |
| 5,300,054 A | 4/1994 | Feist et al. | ............ | 604/378 |
| 5,300,055 A | 4/1994 | Buell | ............ | 604/385.1 |
| 5,304,161 A | 4/1994 | Noel et al. | ............ | 604/378 |
| 5,330,456 A | 7/1994 | Robinson | ............ | 604/368 |
| 5,348,547 A | 9/1994 | Payne et al. | ............ | 604/378 |
| 5,363,604 A | 11/1994 | Heyer | ............ | 51/536 |
| 5,364,382 A | 11/1994 | Latimer et al. | ............ | 604/378 |
| 5,366,451 A | 11/1994 | Levesque | ............ | 604/378 |
| 5,382,245 A | 1/1995 | Thompson et al. | ............ | 604/367 |
| 5,397,316 A | 3/1995 | LaVon et al. | ............ | 604/369 |
| 5,401,267 A | 3/1995 | Couture-Dorschner et al. | ............ | 604/384 |
| 5,409,768 A | 4/1995 | Dickenson et al. | ............ | 428/283 |
| 5,423,786 A | 6/1995 | Fung et al. | ............ | 604/367 |
| 5,429,629 A | 7/1995 | Latimer et al. | ............ | 604/378 |
| 5,439,458 A | 8/1995 | Noel et al. | ............ | 604/378 |
| 5,447,506 A | 9/1995 | Lindquist | ............ | 604/374 |
| 5,460,622 A | 10/1995 | Dragoo et al. | ............ | 604/378 |
| 5,466,232 A | 11/1995 | Cadieux et al. | ............ | 604/378 |
| 5,486,167 A | 1/1996 | Dragoo et al. | ............ | 604/384 |
| 5,514,104 A | 5/1996 | Cole et al. | ............ | 604/366 |
| 5,514,120 A | 5/1996 | Johnston et al. | ............ | 604/378 |
| 5,525,407 A | 6/1996 | Yang | ............ | 428/218 |
| 5,527,171 A | 6/1996 | Soerensen | ............ | 425/83.1 |
| 5,536,555 A * | 7/1996 | Zelazoski et al. | | |
| H1585 H | 8/1996 | Ahr | ............ | 604/378 |
| 5,562,650 A | 10/1996 | Everett et al. | ............ | 604/378 |
| 5,589,117 A | 12/1996 | Yang | ............ | 264/113 |
| 5,593,399 A | 1/1997 | Tanzer et al. | ............ | 604/368 |
| 5,620,430 A | 4/1997 | Bamber | ............ | 604/385.2 |
| 5,637,106 A | 6/1997 | Mitchel et al. | ............ | 604/368 |
| 5,641,441 A | 6/1997 | Yang | ............ | 264/113 |
| 5,647,862 A | 7/1997 | Osborn, III et al. | ............ | 604/378 |
| 5,647,863 A | 7/1997 | Hammons et al. | ............ | 604/378 |
| 5,669,895 A | 9/1997 | Murakami et al. | ............ | 604/380 |
| 5,695,487 A | 12/1997 | Cohen et al. | ............ | 604/384 |
| 5,718,699 A | 2/1998 | Brisebois | ............ | 604/385.1 |
| 5,752,945 A | 5/1998 | Mosley et al. | ............ | 604/370 |
| 5,797,894 A | 8/1998 | Cadieux et al. | ............ | 604/378 |
| 5,817,079 A | 10/1998 | Bergquist et al. | ............ | 604/378 |
| 5,820,973 A | 10/1998 | Dodge, II et al. | ............ | 428/212 |
| 5,827,253 A | 10/1998 | Young et al. | ............ | 604/369 |
| 5,827,254 A | 10/1998 | Trombetta et al. | ............ | 604/378 |
| 5,843,064 A | 12/1998 | Koczab | ............ | 604/378 |
| 5,855,572 A | 1/1999 | Schmidt | ............ | 604/378 |
| 5,866,242 A | 2/1999 | Tan et al. | ............ | 428/219 |
| 5,879,343 A | 3/1999 | Dodge, II et al. | ............ | 604/378 |
| 5,883,231 A | 3/1999 | Achter et al. | ............ | 530/362 |
| 5,910,137 A | 6/1999 | Clark et al. | ............ | 604/387 |
| 5,916,670 A | 6/1999 | Tan et al. | ............ | 428/219 |
| 5,922,163 A | 7/1999 | Helynranta et al. | ............ | 156/296 |
| 6,348,253 B1 * | 2/2002 | Daley et al. | | |
| 6,409,883 B1 * | 6/2002 | Makolin et al. | | |

FOREIGN PATENT DOCUMENTS

| | | | | |
|---|---|---|---|---|
| EP | 0 633 009 | 1/1995 | ............ | A61F/13/15 |
| EP | 0 729 735 | 9/1996 | ............ | A61F/13/15 |
| EP | 0 640 330 | 5/2000 | ............ | A61F/13/46 |
| GB | 2272916 | 6/1994 | ............ | A61F/13/15 |
| GB | 2280115 | 1/1995 | ............ | A61F/13/15 |
| GB | 2284551 | 6/1995 | ............ | A61F/13/15 |
| WO | 89/10109 | 11/1989 | ............ | A61F/13/16 |
| WO | 90/05808 | 5/1990 | ............ | D21H/11/00 |
| WO | 90/11170 | 10/1990 | ............ | B27K/3/00 |
| WO | 90/11171 | 10/1990 | ............ | B27K/3/00 |
| WO | 90/11181 | 10/1990 | ............ | B32B/5/16 |
| WO | 90/11184 | 10/1990 | ............ | B32B/31/00 |
| WO | 91/10413 | 7/1991 | ............ | A61F/5/44 |
| WO | 93/03699 | 3/1993 | ............ | A61F/13/15 |
| WO | 94/02092 | 2/1994 | ............ | A61F/13/15 |
| WO | 94/16558 | 8/1994 | ............ | A61F/13/15 |
| WO | 98/13003 | 4/1998 | ............ | A61F/13/15 |
| WO | 98/22066 | 5/1998 | ............ | A61F/13/15 |
| WO | 98/22067 | 5/1998 | ............ | A61F/13/15 |
| WO | 98/24392 | 6/1998 | ............ | A61F/13/15 |
| WO | 98/24960 | 6/1998 | ............ | D04H/1/54 |
| WO | 98/33464 | 8/1998 | ............ | A61F/13/15 |
| WO | 98/47456 | 10/1998 | ............ | A61F/13/15 |
| WO | 98/51250 | 11/1998 | ............ | A61F/13/15 |
| WO | 99/48454 | 9/1999 | ............ | A61F/13/15 |
| WO | 99/63922 | 12/1999 | ............ | A61F/13/15 |
| WO | 99/63923 | 12/1999 | ............ | A61F/13/15 |
| WO | 99/63925 | 12/1999 | ............ | A61F/13/46 |

* cited by examiner

PERSONAL CARE PRODUCTS HAVING REDUCED LEAKAGE

This application claims the benefit of U.S. Provisional Application No. 60/159,352, filed Oct. 14, 1999.

FIELD OF THE INVENTION

The invention is related to absorbent personal care products. More particularly, it concerns absorbent disposable articles such as feminine care napkins, diapers and training pants, wound care dressings and bandages, and adult incontinence products.

BACKGROUND OF THE INVENTION

Personal care products typically are made with a top sheet material (also referred to as a cover sheet or liner) an absorbent core and a liquid impervious back sheet. Some may also have a surge layer or other specialized layers between the top sheet and absorbent core.

An ideal feminine care product would have no leakage and deliver comfort and discretion to the user. Current feminine care products have relatively high leakage and thus offer only modest protection to the consumer. However, a leak is rather arbitrarily defined in the art and thus consumer perceived leakage is much less. Severe leakage occurs much less frequently.

In the art, a leak is defined as menstrual discharge which stains, contacts or discolors the underwear. All leakage is categorized by three key causes: fluid does not absorb into the product, fluid is absorbed into the product but subsequently leaves it, or fluid never contacts the product. The specific reasons for this leakage may be expressed further in terms of definitive mechanisms. For instance, it may not have suitable space for absorption due to localized saturation or low contact area of the product. It may not have a suitable driving force for absorption because the pores do not have the right balance of permeability and capillarity. The interfiber spaces may be partially full of fluid. Fluid may contact the pad and run-off. The fluid may be too viscous or the pores or interfiber spaces are not large enough to allow fluid to pass.

Various product attempts have been defined to reduce leakage. For instance, wings were developed to cover the underwear and thus reduce leakage by reducing the area of the underwear that could be soiled or contacted. Others have defined emboss lines or shaping lines which cause the pad to fold in a predefined manner to concentrate fluid loading in a specific area or to increase the contact area of the pad with the body. Still others have attempted to reduce leakage by focusing on side or edge leakage presumably caused by compression of the pad by the legs thereby reducing the contact area of the target zone. These product designs have focused on keeping absorbed fluid away from the edges of the product and directing it toward the center. In many cases this is a function not only of the assembly of materials of different size and shape but also their ability to conform to and contact the body in predefined ways.

In all cases, the material systems and their concentration in a specific product design dramatically impact leakage. In the field of material systems design, leakage is a function of materials shaping and conformability as well as intake, distribution, retention and transfer.

For the purpose of this invention, intake is the absorption of body exudates over the lifetime of the product. As such it includes the initial absorption of fluid into a dry product as well as the continued uptake of that fluid into the absorbent structure. Development of superior intake systems requires an understanding of environmental conditions including the nature of the fluid and its discharge. Developing functional intake structures requires an understanding of material characteristics and their interaction with the fluid as components and systems of components including interfaces and product design. Product design includes the arrangement and geometric design of material components and their interaction with the body and fluid.

The environmental conditions surrounding the characteristics of menstrual fluid and its expulsion from the body are well understood in the art. It is this understanding which has permitted the development of suitable intake structures. Menses is a complex, heterogeneous fluid composed of plasma, red blood cells, mucin and tissue/debris. The menses simulant described in this text replicates a specific range of real menstrual fluid properties. The viscosity and elasticity of menstrual fluid span a range of 0 to 1.5 Poise and an elastic stress of 0 to 1.5 dynes/cm$^2$.

It has been found that continuous flow insults in feminine hygiene products average 1 ml/hr and are not literally continuous or constant, but rather variable in rate and may even pause during a cycle. "Gush flow" is defined as a sudden heavy flow condition and occurs at flow rates of from 0.2 to 1 ml/sec or higher. During a gush, 1–5 ml of fluid is released from the body onto the product. The term "continuous flow" is used to define any flow which falls outside of the definition of gush flow. Combining continuous and gush flow conditions results in variable flow. Essentially, "variable flow" is defined as continuous flow with intermittent gush flow occurrences. The response to this problem is termed "variable flow management" and is defined as the ability to absorb and contain continuous and light flow (1–2 ml/hr) as well as multiple gushes or sudden heavy flow insults (0.5 ml/sec with a total volume of 1–5 ml) over the life of the product. In considering environmental conditions, one must also make note of the temperature, humidity, anatomy, activity, characteristics of skin and pubic hair as well as characteristics of undergarments.

Initial intake of menstrual fluid into an absorbent article is a function of the characteristics of the liner or topsheet material and the upper absorbent composite. Intake of menstrual fluid into these materials is a function of the material characteristics including the ratio of to void volume of fiber surface area, fiber orientation and fiber surface wettability. These intrinsic material characteristics specifically define the more familiar material properties of permeability, capillarity and fiber wettability which can be easily calculated and measured by techniques well known in the art. Suitable liner material characteristics are well defined in the art. These have primarily taken the form of apertured film and nonwoven covers and multi-layer composites thereof. Apertured film covers which range from structures having high permeability and low capillarity to those with high permeability and high capillarity. Nonwoven covers typically have much lower permeability with higher levels of capillarity. Regardless of the characteristics of the liner, a suitable absorbent core must be matched to it to permit fluid communication and transfer and thus good fluid intake. Both the interface between the cover and absorbent core as well as the material characteristics are important. Several researchers have defined suitable intake structures for absorption of fluids for personal care articles. For instance, Latimer et. al. (5,364,382) teaches an absorbent article having a retention and surge portion. The surge portion of the invention was defined to uptake and hold at least three successive surges of fluid and direct each to target zone and release it to the retention portion. Dodge, II et al. 20 (WO 98/22066) describes a wettable web of fibers of at most 30 microns in diameter and a permeability of 250 to 1500 Darcy's, a capillary tension of 1.5 to 5 cm and which maintains that permeability and capillarity over the life of the web. Burnes et al. (U.S. patent application Ser. No. 09/072,172) defines an absorbent which wicks artificial menses according to a horizontal wicking test a distance of at least about 1 inch in less than about five minutes. It also denotes as a dependent claim that such fabrics have a density less than 0.15 g/cc.

Intake alone is insufficient in defining absorbency. Absorbent products must also be able to contain the body exudate in such a way as to keep the wearer comfortable and protected from fluid being expressed back onto the wearer or the undergarments. Such materials, particularly for feminine hygiene product usage, can be somewhat stiff and uncomfortable. The layers of these products are usually made from polymer fibers and films, and the absorbent core layer is usually made from wood pulp and superabsorbent particles that swell when wetted. In addition to the issue of comfort, such structures often do not allow fluid movement throughout, thus filling or overfilling the portion of the product in the area where an insult is typically delivered. Attempts have been made to address the movement of fluid in personal care products, again with the use of polymer fibers and the like.

There remains a need for a personal care product that is able to contain the body exudates in such a way as to keep the wearer comfortable and protected from fluid being expressed back onto the wearer or the undergarments. This is an object of this invention.

SUMMARY OF THE INVENTION

The objects of the invention are achieved by an absorbent system that not only takes in fluid, but then transfers that fluid further beneath the first composite. This is achieved in this invention through paired permeability, capillarity, and void volume of the first and second composites. The invention is an absorbent system composed of at least two absorbent composites that have complementary structural/surface energy characteristics. Such an absorbent system has a first absorbent Composite A which has a first permeability, a first capillarity, and a first void volume and at least one second absorbent Composite B which has a second capillarity and a second porosity multiplied by second thickness. The first absorbent Composite A is in liquid communication or contact with at least one second absorbent Composite B, such that the first absorbent Composite A, and the second absorbent Composite B have a fluid partitioning amount in Composite A, a third triple intake time (IT3) and a rewet value. Note that capillarity is measured in units of centimeters of saline as described in the test methods section below.

It is preferred that Composite A have a capillarity which is less than 7.8, a void volume which is not less than 0.09 $cc/cm^2$ and not more than 0.51 $cc/cm^2$ and a permeability greater than 150 darcies, that Composite B have a porosity multiplied by thickness greater than 2.1, hat the difference in capillarity between Composite A and B (CTB-CTA) be greater than 1, that the fluid partitioning amount in Composite A be less than about 22 percent, the third triple intake time be less than 40 seconds and rewet value be less than 0.28 grams.

The invention also pertains to the use of these absorbent systems in absorbent articles for personal care or wound care to promote rapid acquisition and retention of viscous or viscoelastic fluids while providing comfort and dryness to the user by transporting fluid away from the user's skin.

DEFINITIONS

Figure 1A:
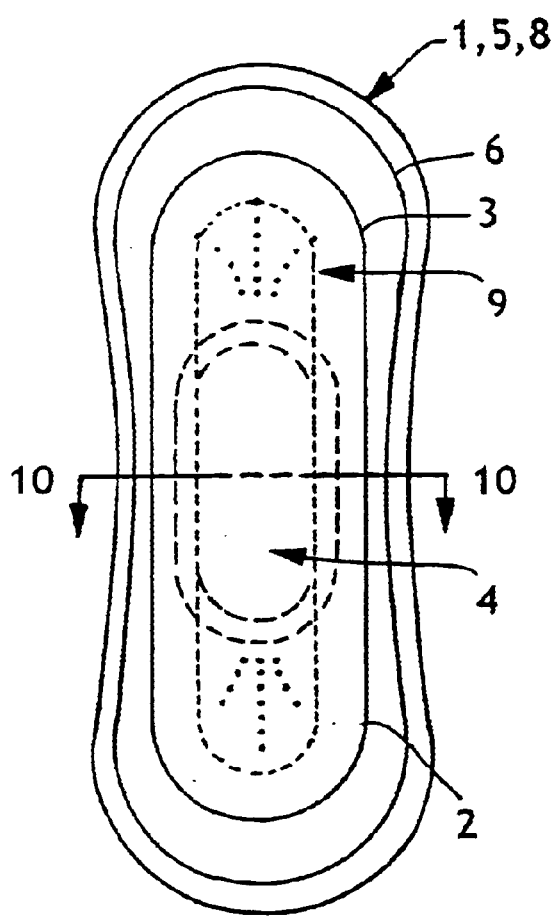
FIG. 1 is a feminine hygiene pad which may contain the absorbent system of the invention.

"Disposable" includes being disposed of after a single use and not intended to be washed and reused.

A "layer" is defined as having a homogeneous composition and density, within typical process variability for nonwoven structures. Alternatively a layer may contain patterns within itself, such as stripes, apertures or waves. "Layer" when used in the singular may have the dual meaning of singular or plural elements.

The "upward" position is closer to the body than "downward" when the article is worn.

"Composite" is defined as having two or more components and may consist of one or more layers. These may be either homogeneous or heterogeneous. It also includes multiple composites which are essentially the same based on structure and surface chemistry.

"Absorbent System" is defined as at least two absorbent composites which have complementary structural/surface energy characteristics and are in part in fluid communication with one another.

As used herein and in the claims, the term "comprising" is inclusive or open-ended and does not exclude additional unrecited elements, compositional components, or method steps.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

"Spunbonded fibers" refers to small diameter fibers that are formed by extruding molten thermoplastic material as filaments from a plurality of fine capillaries of a spinneret. Such a process is disclosed in, for example, U.S. Pat. No. 4,340,563 to Appel et al. The fibers may also have shapes such as those described, for example, in U.S. Pat. No. 5,277,976 to Hogle et al. which describes fibers with unconventional shapes.

"Bonded carded web" refers to webs that are made from staple fibers which are sent through a combing or carding unit, which separates or breaks apart and aligns the staple fibers in the machine direction to form a generally machine direction-oriented fibrous nonwoven web.

"Pattern bonding" is a method wherein heated calender rolls or ultrasonic bonding equipment are used to bond fibers together, usually in a localized bond pattern, though the web can be bonded across its entire surface if so desired. One example of a pattern is the Hansen Pennings or "HP" pattern with about a 30% bond area with about 200 bonds/square inch as taught in U.S. Pat. No. 3,855,046 to Hansen and Pennings. The HP pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern, which produces a 15% bond area. Numerous other bonding patterns exist. Another suitable and well-known bonding method, particularly when using conjugate staple fibers, is through-air bonding, wherein hot air is passed through the web, at least partially melting a component of the web to create bonds.

"Airlaying" is a well-known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. Airlaying is taught in, for example, U.S. Pat. No. 4,640,810 to Laursen et al.

"Personal care product" means diapers, training pants, absorbent underpants, adult incontinence products, feminine hygiene products, wound care items like bandages, and other articles.

"Feminine hygiene products" means sanitary napkins or pads, tampons and panty-liners.

"Target area" refers to the area or position on a personal care product where an insult is normally delivered by a wearer.

TEST METHODS

Material caliper (thickness): The caliper or thickness of a material, in millimeters, is measured at three different pressures; 0.05, 0.20 and 0.50 Psi, using a Frazier spring model compresometer #326 bulk tester with a 2 inch (50.8 mm) foot (Frazier Precision Instrument Corporation, 925 Sweeney Drive, Hagerstown, Md. 21740). Each type of sample is subjected to five repetitions of testing and the results are averaged to produce a single value.

Density: The density of the materials is calculated by dividing the weight per unit area of a sample in grams per square meter (gsm) by the material caliper in millimeters (mm) at 0.05 psi (3.5 g/cm$^2$) and multiplying the result by 0.001 to convert the value to grams per cubic centimeter (g/cc). A total of three samples would be evaluated and averaged for the density values.

Flat System Testing Procedure

Purpose: To determine the fluid handling characteristics of various absorbent systems through analysis of stain length, saturation capacity, and fluid loading of the system components.

Equipment: Hourglass-shaped acrylic plates approximately 8 inch (30.3 cm) long by 3 inch (7.6 cm) wide at the widest parts and 2.5 inch (6.4 cm) wide at the narrowest point, with a 0.25 inch (6.35 mm) hole in the center, weighing approximately 330 grams; syringes; ⅛ in. I. D. Tygon tubing; pipette pump; menses simulant as prepared below; laboratory balance (accurate to 0.00 g).

Preparation:
1) Cut components to desired shape (see test options in Examples for sizes).
2) Weigh and measure bulk thickness of each component and record.
3) Assemble the individual components into the desired component system keeping the marked sections aligned. Label one end as the top. Composite A should be place on top of Composite B and any additional absorbents should be placed below Composite B.
4) Fill the syringes with menses simulant and attach Tygon tubing to syringes.
5) Place syringes in pipette pump.
6) Program pump (currently using 30 cc syringes dispensing 10 ml of simulant in one hour).
7) With the open ends of the tubing placed in a beaker, prime tubing by infusing (running) pump until all air is out of tubing and simulant is exiting the tubing at the insult end.
8) Program pump; the flow protocol calls for 30 ml/min for 2 seconds followed by 5 ml/hr for 14 minutes and 58 seconds. This flow sequence is then repeated 4 times for a total of 60 minutes and approximately 9 ml of fluid.
9) Place the component systems to be tested near the pipette pump, insert the free end of one tubing into the hole in the acrylic plate and place the acrylic plate centered on top of the system.
10) Start the pipette pump to begin the insult.
11) At the end of the insult period, remove the tubing and acrylic plates. Take photos of the component system and composites and print.
12) Weigh each composite individually and record the weight. The weight in the upper composite is termed the fluid partitioning amount in the intake/retention/transfer composite wherein larger amounts of fluid denote less transfer and lower amounts of fluid denote better transfer.
13) Measure and record the stain length for each composite.
14) Enter the data in a spreadsheet for graphing and analysis.

Triple Intake Rewet/Test Procedure (TIR): The objective of this test is to determine differences between materials and/or material composites in the rate of intake and the amount of fluid flow back to the surface under pressure when 3 fluid insults are applied, with time allowed for fluid to distribute in the material(s) between insults.

Figure 3:
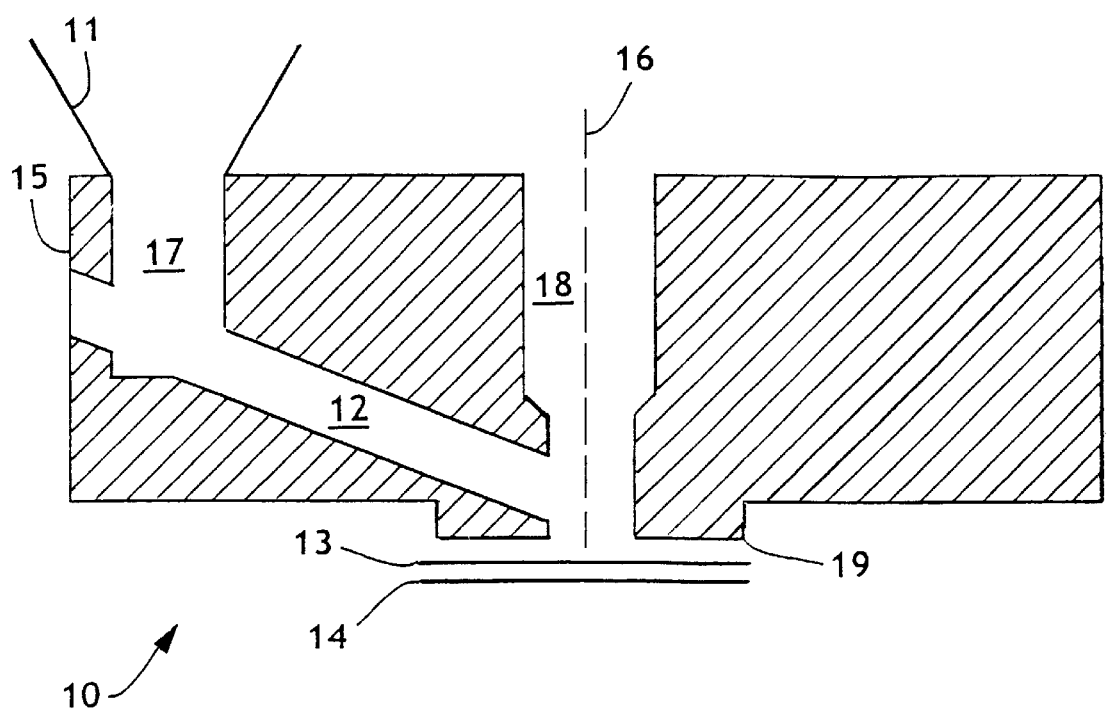
FIG. 3 is a schematic diagram of a rate block apparatus suitable for use in determining fluid intake time of a material or material system.

Equipment Needed:
2 acrylic rate blocks as shown in FIG. 3. The test apparatus consists of a clear, preferably acrylic, rate block 10 as shown in FIG. 3. The rate block 10 is 3 inches (76.2 mm) wide and 2.87 inches (72.9 mm) deep (into the page) and has an overall height of 1.125 inches (28.6 mm) which includes a center area 19 on the bottom of the rate block 10 that projects farther from the main body of the rate block 10 and has a height of 0.125 inches (3.2 mm) and a width of 0.886 inches (22.5 mm). The rate block 10 has a capillary 12 with an inside diameter of 0.186 inches (4.7 mm) that extends diagonally downward from one side 15 to the center line 16 at an angle of 21.8 degrees from the horizontal. The capillary 12 may be made by drilling the appropriately sized hole from the side 15 of the rate block 10 at the proper angle beginning at a point 0.726 inches (18.4 mm) above the bottom of the rate block 10; provided, however, that the starting point of the drill hole in the side 15 must be subsequently plugged so that test fluid will not escape there. The top hole 17 has a diameter of 0.312 inches (7.9 mm), and a depth of 0.625 inches (15.9 mm) so that it intersects the capillary 12. The top hole 17 is perpendicular to the top of the rate block 10 and is centered 0.28 inches (7.1 mm) from the side 15. The top hole 17 is the aperture into which the funnel 11 is placed. The center hole 18 is for the purpose of viewing the progression of the test fluid and is actually of an oval shape into the plane of FIG. 3. The center hole 18 is centered width-wise on the rate block 10 and has a bottom hole width of 0.315 inches (8 mm) and length of 1.50 inches (38.1 mm) from center to center of 0.315 inch (8 mm) diameter semi-circles making up the ends of the oval. The oval enlarges in size above 0.44 inches (11.2 mm) from the bottom of the rate block 10, for ease of viewing, to a width of 0.395 inches (10 mm) and a length of 1.930 inches (49 mm). The top hole 17 and center hole 18 may also be made by drilling.

P-5000 pipette with RC-5000 tips and foam pipette insert.

Small beaker

Menses simulant (made according to directions below) warmed in bath at 25° C. for 30 minutes or more Small spatula (stirrer)

Bench liner 2 stopwatches

1–2 timers

Gauze squares for cleaning simulant

Procedure: Lay out sample composites according to materials testing plan.

Ply composites are as follows:
  Top: Cover—3.5 dpf, 0.6 osy polypropylene spunbond at 0.08 g/cc. Topically treated with 0.3% AHCOVEL®. (Note for commercial products—Always® and Kotex®, the commercial cover was replaced with this cover to observe effects of the absorbent core)
  Middle: Composite A
  Bottom: Composite B and/or additional absorbent cores (If a transfer delay layer or composite (TDL) is present it is placed in between Composite A and B)

1. Weigh each composite dry, record weight. Ply materials back into original configuration.
2. Weigh a dry blotter, record weight and also mark weight on blotter.
3. Place acrylic rate block in middle of sample system.
4. Calibrate pipette:
   Weigh a small empty beaker on the balance.
   Set pipette to 2 mls.
5. Draw simulant into pipette.
   Deliver simulant from pipette into beaker.
   If balance indicates 2 grams of simulant was delivered, setting is correct.
   If more or less than 2 grams was delivered, decrease or increase the setting and repeat adjusting pipette and weighing the amount of simulant delivered until 2 grams is delivered.

Simulant Handling:

Remove simulant from the refrigerator 30 minutes to 1 hour before using and warm in water bath. Before cutting bag nozzle, massage the bag between hands for a few minutes to mix the simulant, which will have separated in the bag. Cut the bag tubing and pour simulant needed into a small beaker. Stir slowly with a small spatula to mix thoroughly. Return bag to the refrigerator if you do not anticipate using all of it. Return bag to water bath if more will be used during the day.

Test:

Step 1: Center acrylic rate block with funnel on sample. Insult sample system with 2 mls. simulant, using stopwatch to measure the time from the start of the insult until the fluid is absorbed beneath the cover material. Record time. Wait 9 minutes from start of insult.

Step 2: For the first sample, repeat Step 1 a second time.

Step 3: For the first sample, repeat Step 1 a third time. This time is referred to as "third triple intake time (IT3)" and is reported in seconds.

"Triple intake rewet time three" (TIR3) and is reported in seconds Step 4: After 3 insults, weigh each individual material and replace in original system configuration, place sample with a blotter on the rewet stand. Apply 1.0 psi pressure for 3 minutes. Record the weight of the wet blotter. Do not weigh the materials after the rewet portion of the test. The amount of fluid absorbed onto the blotter is termed the rewet value. Low values of rewet are preferred and can be associated with a product or absorbent system which retains (does not expel) more fluid in its structure under applied loads.

Permeability

Permeability (k) was calculated using the Kozeny-Carman equation. This is a widely used method. The reference for the Kozeny constant which was used is found in "Some Principles of Flow and Their Application to Paper" by Hoyland in Paper Technology and Industry, December 1976, p 292.

| Calculated Variable | Dimensions |
| --- | --- |
| $k = \dfrac{\varepsilon^3}{KS_0^2(1-\varepsilon)^2} \dfrac{1}{9.87 \times 10^{-9}}$ | Darcys |
| $K = \dfrac{3.5\varepsilon^3}{(1-\varepsilon)^{0.5}}[1 + 57(1-\varepsilon)^3]$ | dimensionless |
| $\alpha = \sum\limits_i \dfrac{x_i}{r_{i,\text{eff}}\,\rho_i}$ | cm$^2$/g |
| $\rho_{\text{avg}} = \left(\sum\limits_i \dfrac{x_i}{\rho_i}\right)^{-1}$ | g/cm$^3$ |
| $S_0 = \alpha\,\rho_{\text{avg}}$ | cm$^{-1}$ |
| $\rho = 1 - \sum\limits_i x_i \dfrac{\rho_{\text{web}}}{\rho_i}$ | dimensionless |
| $r_{i,\text{eff}} = \dfrac{V_i}{SA_i}$ | cm |
| $\rho_{\text{web}} = \dfrac{BW}{10^4 t}$ | g/cm$^3$ | for long cylinders $$r_{i,\text{eff}} = \dfrac{\dfrac{\pi d_i^2 L}{4}}{\pi d_i L} = \dfrac{d_i}{4 \times 10^4}$$

for spheres $$r_{i,eff} = \frac{\frac{4}{3}\frac{\pi d_i^3}{8}}{\pi d_i^2} = \frac{d_i}{6 \times 10^4}$$

| Inputs | | |
|---|---|---|
| $d_i$ | = | diameter of component i ($\mu$m) |
| $\rho_i$ | = | density of component i (g/cm$^3$) |
| $x_i$ | = | mass fraction of component i in web |
| BW | = | weight of the sample/area (g/m$^2$) |
| t | = | thickness of sample under 0.05 psi (23.9 dyne/cm$^2$) or 2.39 Pascal (N/m$^2$) load |

Permeability Example Calculation

For a structure contains 60% NB416 southern softwood and 25% 6 denier PET and 15% 2.8 denier PE/PET sheath/core binder fiber, a basis weight of 100 g/m$^2$ and a bulk thickness of 0.167 cm under a 0.05 psi load, the example permeability calculation follows. The component properties are:

| Component | Shape | Diameter ($\mu$m) | Density (g/cm$^3$) |
|---|---|---|---|
| Southern softwood | Cylinder | 13.3 | 1.55 |
| 6 denier PET | Cylinder | 24.8 | 1.38 |
| 2.8 denier PE/PET | Cylinder | 18.5 | 1.16 |

$$\rho_{web}(g/cm^3) = \frac{BW}{10^4 t}$$

$$\rho_{web}(g/cm^3) = \frac{100}{(0.167)10^4}$$

$$\rho_{web}(g/cm^3) = 0.06$$

$$\rho = 1 - \rho_{web}\sum_i \frac{x_i}{\rho_i}$$

$$\rho = 1 - 0.06\left(\frac{0.60}{1.55} + \frac{0.25}{1.38} + \frac{0.15}{1.16}\right)$$

$$\rho = 0.9581$$

$$\alpha(cm^2/g) = \sum_i \frac{x_i}{r_{i,eff}\rho_i}$$

$$\alpha(cm^2/g) = \frac{0.60}{\left(\frac{13.3}{4\times10^4}\right) \times 1.55} + \frac{0.15}{\left(\frac{18.5}{4\times10^4}\right) \times 1.16} + \frac{0.25}{\left(\frac{24.8}{4\times10^4}\right) \times 1.38}$$

$$\alpha(cm^2/g) = 1736$$

$$\rho_{avg}(g/cm^3) = \left(\sum_i \frac{x_i}{\rho_i}\right)^{-1}$$

$$\rho_{avg}(g/cm^3) = \left(\frac{0.60}{1.55} + \frac{0.15}{1.16} + \frac{0.25}{1.38}\right)^{-1}$$

$$\rho_{avg}(g/cm^3) = 1.434$$

$$S_0(cm^{-1}) = \alpha\, \rho_{avg}$$

$$S_0(cm^{-1}) = 1736 \times 1.434$$

$$S_0(cm^{-1}) = 2489$$

$$K = \frac{3.5\varepsilon^3}{(1-\varepsilon)^{0.5}}[1 + 57(1-\varepsilon)^3]$$

$$K = \frac{3.5(0.9581)^3}{(1-0.9581)^{0.5}}[1 + 57(1-0..9581)^3]$$

$$K = 15.10$$

$$k = \frac{\varepsilon^3}{KS_0^2(1-\varepsilon)^2}\frac{1}{9.87 \times 10^{-9}}$$

$$k = \frac{(0.9581)^3}{(15.10)(24\,89)^2(1-0.9581)^2}\frac{1}{9.87 \times 10^{-9}}$$

$$k = 542\ Darcys$$

Capillary Tension Calculation Method

The capillary tension is found by equating the capillary pressure to the hydrostatic pressure. The capillary tension is expressed in units of cm saline. This may be found in *Absorbency* by Pronoy Chatterjee (ed.) Elsevier Science Publishing Company Inc., 1985 p. 39.

| Variable | | Dimensions |
|---|---|---|
| $c.t. = \frac{2}{\sqrt{\pi}} \frac{\gamma}{\left(\frac{1}{\rho_{web}} - \frac{1}{\rho_{avg}}\right)} \frac{\alpha}{980}$ | | cm saline |
| $\alpha = \sum_i \frac{x_i}{r_i \rho_i}\cos(\theta)$ | | cm$^2$/g |
| $\rho_{avg} = \left(\sum_i \frac{x_i}{\rho_i}\right)^{-1}$ | | g/cm$^3$ |
| $r_{i,eff} = \frac{V_i}{SA_i}$ | | cm | for long cylinders $$r_{i,eff} = \frac{\frac{\pi d_i^2 L}{4}}{\pi d_i L} = \frac{d_i}{4 \times 10^4}$$

for spheres $$r_{i,eff} = \frac{\frac{4}{3}\frac{\pi d_i^3}{8}}{\pi d_i^2} = \frac{d_i}{6 \times 10^4}$$

Inputs
  $\gamma$=surface tension of fluid (dyne/cm)
  $d_i$=diameter of component i ($\mu$m)
  $\rho_i$=density of component i (g/cm$^3$)
  $x_i$=mass fraction of component i in web
  $\rho_{web}$=density of web (g/cm$^3$)
  BW=weight of sample/area (g/m$^2$)
  t=thickness of sample under 0.05 psi (23.9 dyne/cm$^2$) or 2.39 Pascal (N/m$^2$) load Capillary Tension Example Calculation For a structure contains 60% NB416 southern softwood and 25% 6 denier PET and 15% 3 denier PE/PET sheath/ core binder fiber, a basis weight of 100 g/m² and a bulk thickness of 0.167 cm at 0.05 psi the example calculation of capillary tension of saline follows. The surface tension of saline is 68 dyne/cm. The component properties are:

| Component | Shape | Diameter ($\mu$m) | Contact Angle | Density ($\mu$m) |
|---|---|---|---|---|
| Southern softwood | Cylinder | 13.3 | 30 | 1.55 |
| 6 denier PET | Cylinder | 24.8 | 60 | 1.38 |
| 2.8 denier PE/PET Variable | Cylinder | 18.5 | 80 | 1.16 |

$$\alpha \ (cm^2/g) = \sum_i \frac{x_i}{r_i \rho_i} \cos(\theta)$$

$$\alpha \ (cm^2/g) = \frac{0.60 \cos(30)}{\left(\frac{13.3}{4 \times 10^4}\right) \times 1.55} + \frac{0.25 \cos(60)}{\left(\frac{24.8}{4 \times 10^4}\right) \times 1.38} + \frac{0.15 \cos(80)}{\left(\frac{18.5}{4 \times 10^4}\right) \times 1.16}$$

$$\alpha \ (cm^2/g) = 1736$$

$$\rho_{avg} \ (g/cm^3) = \left(\sum_i \frac{x_i}{\rho_i}\right)^{-1}$$

$$\rho_{avg} \ (g/cm^3) = \left(\frac{0.40}{1.55} + \frac{0.25}{1.38} + \frac{0.15}{1.16}\right)^{-1}$$

$$\rho_{avg} \ (g/cm^3) = 1.434$$

$$\rho_{web} \ (g/cm^3) = \frac{BW}{10^4_t}$$

$$\rho_{web} \ (g/cm^3) = \frac{100}{(0.167)10^4}$$

$$\rho_{web} \ (g/cm^3) = 0.06$$

$$c.t. \ (cm \ saline) = \frac{2}{\sqrt{\pi}} \sqrt{\frac{\gamma}{\left(\frac{1}{\rho_{web}} - \frac{1}{\rho_{avg}}\right)} \frac{\alpha}{980}}$$

$$c.t. \ (cm \ saline) = \frac{2}{\sqrt{\pi}} \sqrt{\frac{68}{\left(\frac{1}{0.06} - \frac{1}{1.434}\right)} \frac{1108}{980}}$$

$$c.t. \ (cm \ saline) = 3.06$$

Artificial Menses Preparation: The artificial menses fluid used in the testing was made according to U.S. Pat. No. 5,883,231 from blood and egg white by separating the blood into plasma and red cells and separating the white into thick and thin portions, where "thick" means it has a viscosity after homogenization above about 20 centipoise at 150 sec⁻¹, combining the thick egg white with the plasma and thoroughly mixing, and finally adding the red cells and again thoroughly mixing. A more detailed procedure follows:

Blood, in this example defibrinated swine blood, is separated by centrifuging at 3000 rpm for 30 minutes, though other methods or speeds and times may be used if effective. The plasma is separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition or anti-coagulant chemicals and others. The blood must be non-coagulating in order to be useful and any method which accomplishes this without damaging the plasma and red cells is acceptable.

Jumbo chicken eggs are separated, the yolk and chalazae discarded and the egg white retained. The egg white is separated into thick and thin portions by straining the white through a 1000 micron nylon mesh for about 3 minutes, and the thinner portion discarded. The thick portion of egg white, which is retained on the mesh, is collected and drawn into a 60 cc syringe, which is then placed on a programmable syringe pump and homogenized by expelling and refilling the contents five times. The amount of homogenization is controlled by the syringe pump rate of about 100 ml/min, and the tubing inside diameter of about 0.12 inches. After homogenizing the thick egg white has a viscosity of about 20 centipoise at 150 sec⁻¹ and is then placed in the centrifuge and spun to remove debris and air bubbles at about 3000 rpm for about 10 minutes After centrifuging, the thick, homogenized egg white, which contains ovamucin, is added to a 300 cc FENWAL® Transfer pack container using a syringe. Then 60 cc of the swine plasma is added to the FENWAL® Transfer pack container. The FENWAL® Transfer pack container is clamped, all air bubbles removed, and placed in a Stomacher lab blender where it is blended at normal (or medium) speed for about 2 minutes. The FENWAL® transfer pack container is then removed from the blender, 60 cc of swine red blood cells are added, and the contents mixed by hand kneading for about 2 minutes or until the contents appeared homogenous. A hematocrit of the final mixture should show a red blood cell content of about 30 weight percent and generally should be at least within a range of 28–32 weight percent for artificial menses made according to this example. The amount of egg white is about 40 weight percent.

The ingredients and equipment used in the preparation of artificial menses are readily available. Below is a listing of sources for the items used, though of course other sources may be used providing they are approximately equivalent.

Blood (swine): Cocalico Biologicals, Inc., 449 Stevens Rd., Reamstown, Pa. 17567, (717) 336-1990.

Fenwal® Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

DETAILED DESCRIPTION

The absorbent composites and absorbent systems of this invention may be made from a variety of processes traditionally used to prepare stabilized nonwoven webs including coform, carding, meltblowing, spunbonded, airlaying, needlepunching, wetlaying, hydroentangling etc. Preferred embodiments of this application are prepared using the airlaid process. The nonwoven airlaid composites may be prepared from a variety of fibers and mixtures of fibers including but not limited to synthetic fibers, natural fibers including hydroentangled pulp, mechanically and chemically softened pulp, staple fibers, slivers, meltblown and spunbond fibers and the like.

The production of airlaid nonwoven composites is well defined in the literature and documented in the art. Example include the DanWeb process as described in U.S. Pat. No. 4,640,810 Laursen et al assigned to Scan Web of North America Inc; the Kroyer process as described in U.S. Pat. No. 4,494,278 Kroyer et al and U.S. Pat. No. 5,527,171 Soerensen assigned to Niro Separation a/s; the method of U.S. Pat. No. 4,375,448 Appel et al assigned to Kimberly-Clark Corporation, or other similar methods. The webs produce by these methods are subsequently bonded together to form an adequate tensile strength web by thermal fusing, latex bonding or combinations thereof, which are well known in the art. Webs produced in this text are best exemplfied but not limited to the Danweb process.

Superabsorbents that are useful in the present inventions can be chosen from classes based on chemical structure as well as physical form. These include superabsorbents with low gel strength, high gel strength, surface cross-linked superabsorbents, uniformly cross-linked superabsorbents, or superabsorbents with varied cross-link density throughout the structure. Superabsorbents may be based on chemistries that include poly(acrylic acid), poly(iso-butylene-co-maleic anhydride), poly(ethylene oxide), carboxy-methyl cellulose, poly(-vinyl pyrrollidone), and poly(-vinyl alcohol). The superabsorbents may range in swelling rate from slow to fast. The superabsorbents may be in the form of foams, macroporous or microporous particles or fibers, particles or fibers with fibrous or particulate coatings or morphology. The superabsorbents may be in the shape of ribbons, particles, fibers, sheets or films. Superabsorbents may be in various length and diameter sizes and distributions. The superabsorbents may be in various degrees of neutralization. Counter-ions are typically Li, Na, K, Ca.

Materials of this invention may include superabsorbents of the types mentioned above. An exemplary superabsorbent was obtained from The Dow Chemical Company and is recognized as AFA-173-60B. An Example of these types of superabsorbents may be obtained from Stockhausen, Inc and is designated FAVOR® SXM 880. An example of fibrous superabsorbents may be obtained from Camelot Technologies, Ltd., of High River, Alberta, Canada and is designated FIBERDRI® 1241. Another Example included in these types of superabsorbents is obtained from Chemtall Inc. or Riceboro, Ga., and is designated FLOSORB 60 LADY®, also known as LADYSORB 60®. Examples of superabsorbents with fibrous or particulate coatings are microcrystalline cellulose coated on FAVOR® 880 and cellulose fiber coated FAVOR® 880. These are described in U.S. Provisional Patent Application 60/129,774. Additional types of superabsorbents not listed here which are commonly available and known to those skilled in the art can also be useful in the present inventions.

Binders typically used in these structures help provide mechanical integrity and stabilization. Binders include fiber, liquid or other binder means which may be thermally activated. Preferred fibers for inclusion are those having a relative melting point such as polyolefin fibers. Lower melting point polymers provide the ability to bond the fabric together at fiber cross-over points upon the application of heat. In addition, fibers having a lower melting polymer, like conjugate and biconstituent fibers are suitable for practice of this invention. Fibers having a lower melting polymer are generally referred to as "fusible fibers". By "lower melting polymers" what is meant are those having a glass transition temperature less than about 175 C. It should be noted that the texture of the absorbent web can be modified from soft to stiff through selection of the glass transition temperature of the polymer. Exemplary binder fibers include conjugate fibers of polyolefins, polyamides and polyesters. Three suitable binder fibers are sheath core conjugate fibers available from KoSa Inc. (Charlotte, N.C.) under the designation T-255 and T-256 or Copolyester designation, though many suitable binder fibers are known to those skilled in the art, and are available by many manufacturers such as Chisso and Fibervisions LLC of Wilmington, Del. A suitable co-polyester binder fiber has been developed by KoSa as a sheath core application and is known by designation T-254 (low melt COPET). A suitable liquid binder is KYMENE® 557LX available from Hercules Inc. of Wilmington, Del. Other suitable liquid binders include ethylene vinyl acetate emulsion polymers sold by National Starch and Chemical Company (Bridgewater, N.J.) under the tradename DUR-O-SET® ELITE® series (including ELITE® 33 and ELITE® 22). Other suitable binder fibers are sold by Air Products Polymers and Chemicals under the name AIRFLEX®.

Synthetic fibers include those made from polyolefins, polyamides, polyesters, rayon, acrylics, superabsorbents, TENCEL® regenerated cellulose and any other suitable synthetic fibers known to those skilled in the art. Synthetic fibers may also include kosmotropes for product degradation.

Many polyolefins are available for fiber production, for example polyethylenes such as Dow Chemical's ASPUN® 6811A liner low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Many other polyolefins are also available.

Particularly preferred materials for this application include polyesters which may range in size or denier from 3 to 25 denier and having various cross-sections including round, pentalobal, helical crimped, etc. Such fibers have been developed by Kosa, Inc. with a durably wettable finish and are known by designation of fiber denier followed by polymer type and cross section. Examples would include 8 dpf, T-224 (High Void); 8 dpf, T-224 (trilobal); 15 dpf T-224 (round); 10 dpf T-224 (round); 6 dpf T-224 (round) and 3 dpf T-224 (round).

Natural fibers include wool, cotton, flax, hemp and wood pulp. Wood pulps include standard softwood fluffing grade such as CR-1654 (U.S. Alliance Pulp Mills, Coosa, Ala.). Pulp may be modified in order to enhance the inherent characteristics of the fibers and their processability. Curl may be imparted to the fibers by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylolated compounds such as urea or urea derivatives, dialdehydes such as maleic anhydride, non-methylolated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HPF2 pulp and still another is IP SUPERSOFT® from International Paper Corporation. Suitable rayon fibers are 1.5 denier Merge 18453 fibers from Tencel Incoporated of Axis, Ala.

This invention defines an absorbent system below the liner that not only takes in fluid, but then transfers that fluid further beneath the first composite. Exemplary intake or surge materials must be combined with complementary absorbent core components in liquid communication with them in order to be effective. When handling menstrual fluid, due to the complex nature of the fluid, care must be taken in defining an absorbent system so that the fluid being desorbed from the liner is transferred to an area away from the liner in order to maintain a clean surface. This is achieved in this invention through paired permeability, capillarity, and void volume of the first and second composites. The invention is an absorbent system composed of at least two absorbent composites which have complementary structural/surface energy characteristics. Such an absorbent system has a first absorbent Composite A: which has a first permeability, a first capillarity, and a first void volume and at least one second absorbent Composite B: which has a second capillarity and a second porosity multiplied by second thickness The first absorbent Composite A is in liquid communication or contact with at least one second absorbent Composite B, such that first absorbent Composite A, and the second absorbent Composite B have a fluid partitioning amount in Composite A, a third triple intake time (IT3) and a rewet value.

It is preferred that Composite A have a capillarity which is less than 7.8, a void volume which is not less than 0.09 cc/cm$^2$ not more than 0.51 cc/cm$^2$ and a permeability greater than 150 darcies, and that Composite B have a porosity multiplied by thickness greater than 2.1, and that the difference in capillarity between Composite A and B (CTB-CTA) be greater than 1, and that the fluid partitioning amount in Composite A is less than about 22 percent, the third triple intake time is less than 40 seconds and rewet value is less than 0.28 grams.

The invention also pertains to the use of these absorbent systems in absorbent articles for personal care or wound care to promote rapid acquisition and retention of viscous or viscoelastic fluids while providing comfort and dryness to the user by transporting fluid away from the user's skin.

In order to evaluate the effectiveness of the invention, numerous examples and comparative examples were made and tested according to the tests described herein. Descriptions of these examples and comparatives follows.

Options refer to sample size used for testing. For the purposes of the Examples, the abbreviation "FST" shall refer to Flat Systems Testing Procedure, and the abbreviation "TIR" shall refer to Triple Intake Rewet Testing Procedure.

EXAMPLE 1

An Absorbent System Comprising Composite A and B that are in Liquid Communication
Composite A:
  (Option 1—2 inch (5.1 cm)×6 inch (15.2 cm) for FST and 1.5 inch (3.8 cm)×3 inch (7.6 cm) for TIR)
  104 gsm, 0.11 g/cc airlaid 40 percent 6 dpf, Polyester T-224, 40 percent Southern Softwood (NB416), 20 percent 2.8 dpf binder fiber (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

EXAMPLE 2

An absorbent system comprising Composite A and B that are in liquid communication
Composite A:
  (Option 1—2 inch (5.1 cm)×6 inch (15.2 cm) for FST and 1.5 inch (3.8 cm)×3 inch (7.6 cm) for TIR)
  194 gsm, 0.12 g/cc airlaid 40 percent 6 dpf, Polyester T-224, 40 percent Southern Softwood (NB416), 20 percent 2.8 dpf binder fiber (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

EXAMPLE 3

An absorbent system comprising Composite A and B that are in liquid communication
ps Composite A:
  (Option 1—2 inch (5.1 cm)×6 inch (15.2 cm) for FST and 1.5 inch (3.8 cm)×3 inch (7.6 cm) for TIR)
  109 gsm, 0.075 g/cc airlaid 40 percent 6 dpf, Polyester T-224, 40 percent Southern Softwood (NB416), 20 percent 2.8 dpf binder fiber (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

EXAMPLE 4

An absorbent system comprising Composite A and B that are in liquid communication
Composite A:
  (Option 1—2 inch (5.1 cm)×6 inch (15.2 cm) for FST and 1.5 inch (3.8 cm)×3 inch (7.6 cm) for TIR)
  203 gsm, 0.07 g/cc airlaid 40 percent 6 dpf, Polyester T-224, 40 percent Southern Softwood (NB416), 20 percent 2.8 dpf binder fiber (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

EXAMPLE 5

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  103 gsm, 0.076 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

EXAMPLE 6

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
208 gsm, 0.074 g/cc airlaid composed of 90 percent Southern Softwood (NB416) and 10 percent 2.8 dpf binder fiber, (T-255) with a wettable surface finish.

Composite B:
(Option 2—1.5 inch (3.8 cm)×3 inch (7.6 cm))
636 gsm, 0.11 g/cc Fluff (Coosa 0054 or NB416)

EXAMPLE 7

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
119 gsm, 0.06 g/cc airlaid composed of 90 percent Buckeye HPZ3 and 10 percent 2.8 dpf binder fiber, (T-255) with a wettable surface finish.

Composite B:
(Option 2—1.5 inch (3.8 cm)×3 inch (7.6 cm))
636 gsm, 0.11 g/cc Fluff (Coosa 0054 or NB416)

EXAMPLE 8

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
A bi-layer airlaid composite which has density and wettability gradients. The top layer is a 50 gsm, 0.06 g/cc of 40 percent Southern Softwood (NB416), 40 percent 6dpf, Polyester T-224 with a wettable finish and 20 percent 2.8 dpf binder fiber (T-255) with a wettable surface finish. The lower layer is 100 gsm, 0.12 g/cc of 90 percent Southern Softwood (NB416) and 10 percent 2.8 dpf binder fiber, (T-255) with a wettable surface finish.

Composite B:
(Option 2—1.5 inch (3.8 cm)×3 inch (7.6 cm))
611gsm, 0.11 g/cc airlaid composed of 90 percent Southern Softwood (NB416) and 10 percent 2.8 dpf binder fiber, (T-255) with a wettable surface finish.

EXAMPLE 9

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
94 gsm, 0.07 g/cc airlaid 40 percent 6 dpf, Polyester T-224, 40 percent Southern Softwood (NB416), 20 percent 2.8 dpf binder fiber (T-255) with a wettable surface finish.

Composite B:
(Option 2—1.5 inch (3.8 cm)×3 inch (7.6 cm))
611 gsm, 0.11 g/cc airlaid composed of 90 percent Southern Softwood (NB416) and 10 percent 2.8 dpf binder fiber, (T-255) with a wettable surface finish.

EXAMPLE 10

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
106 gsm, 0.08 g/cc airlaid 40 percent 6 dpf, Polyester T-224, 40 percent Southern Softwood (NB416), 20 percent 2.8 dpf binder fiber (T-255) with a wettable surface finish.

Composite B:
(Option 2—1.5 inch (3.8 cm)×3 inch (7.6 cm))
630 gsm, 0.13 g/cc airlaid composed of 80 percent Southern Softwood (NB416), 10 percent superabsorbent particulate AFA-173-60B and 10 percent 2.8 dpf binder fiber, (T-255) with a wettable surface finish.

EXAMPLE 11

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
191 gsm, 0.07 g/cc airlaid 40 percent 6 dpf, Polyester T-224, 40 percent Southern Softwood (NB416), 20 percent 2.8 dpf binder fiber (T-255) with a wettable surface finish.

Composite B:
(Option 2—4.5" (11.4 cm)×3 inch (7.6 cm) for FST and TIR)
611 gsm, 0.12 g/cc airlaid composed of 90 percent Southern Softwood (NB416) and 10 percent 2.8 dpf binder fiber, (T-255) with a wettable surface finish.

EXAMPLE 12

An absorbent system comprising Composite A and B that are in liquid communication.

Composite A:
(Option 1—2 inch (5.1 cm)×6 inch (15.2 cm) for FST and 1.5 inch (3.8 cm)×3 inch (7.6 cm) for TIR)
182 gsm, 0.07 g/cc airlaid composed of 90 percent Southern Softwood (NB416) and 10 percent 2.8 dpf binder fiber, (T-255) with a wettable surface finish.

Composite B:
(Option 2—4.5" (11.4 cm)×3 inch (7.6 cm) for FST)
611 gsm, 0.12 g/cc airlaid composed of 90 percent Southern Softwood (NB416) and 10 percent 2.8 dpf binder fiber, (T-255) with a wettable surface finish.

Product Examples

Figure 1B:
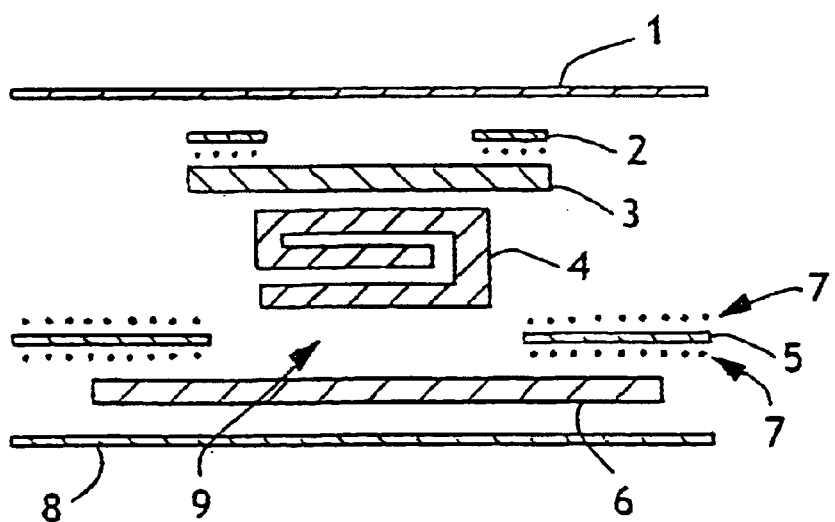

Examples 13–16 refer to FIG. 1.

FIG. 1 contains a plan view (1A) and a cross-sectional view (1B) taken along line 10—10, of an absorbent pad. The absorbent pad has a cover 1, an impermeable barrier 5 and a baffle 8 that are the same size. The pad has a pink cue 2, and an upper absorbent 3 over an absorbent pledget 4. The absorbent pledget 4 is above the impermeable barrier 5 which has a hole 9 cut into it. The bottom absorbent 6 is below the impermeable barrier 5 and above the baffle 8 that protects the wearer's clothing. Construction adhesive 7 in the amount of between 10 and 15 gsm is used to bond the barrier 5 to the layers on either side of it. The materials of construction are described in more detail in Examples 13–16.

EXAMPLE 13

Example 13 is an integrated 3 dimensional composite that consisted of a substrate or base layer with integrated ridge or hills attached on the surface. Such materials are believed to be particularly suitable for intake and fluid transfer. The substrate layer was 100 gsm, 0.12 g/cc and was composed of 90 percent Southern Softwood (NB416) and 10 percent 2.8 dpf binder fiber, (T-255) with a wettable surface finish). The ridges or hills were composed of 100 gsm, about 0.04 g/cc 40 percent 6 dpf, Polyester T-224, 40 percent Southern Softwood (NB416), 20 percent 2.8 dpf binder fiber (T-255) with a wettable surface finish.

| | |
|---|---|
| Cover or Topsheet | 3.5 dpf, 0.6 osy Polypropylene Spunbond (92 percent Union Carbide E5D47 PP (polypropylene) and 8 percent AMPACET ® 41438 TiO$_2$ (50 percent concentrate) and point bonded using Hansen & Pennings (HP) pattern. Web was topically treated to 0.3 percent AHCOVEL ® Base N62 (ICI Surfactants, Delaware). |
| Pink Cue | 2.8 dpf, 0.8 osy polypropylene spunbond treated with 0.3 percent AHCOVEL ® Base N62 (ICI Surfactants, Wilmington, Delaware) |
| Upper Absorbent Material | A bi-layer airlaid composite which has density and wettability gradients. The top layer is a 50 gsm, 0.06 g/cc of 40 percent Southern Softwood (NB416), 40 percent 6 dpf, Polyester T-224 with a wettable finish and 20 percent 2.8 dpf binder fiber (T-255) with a wettable surface finish. The lower layer is 100 gsm, 0.12 g/cc of 90 percent Southern Softwood (NB416) and 10 percent 2.8 dpf binder fiber, (T-255) with a wettable surface finish. |
| Absorbent Material Pledget | E-folded pledget 204 gsm (note that this is really 612 gsm, applying our definition of composite and assuming that e-folded implies that there are three layers of same material composition), 0.11 g/cc airlaid composed of 90 percent Southern Softwood (NB416) and 10 percent 2.8 dpf binder fiber, (T-255) with a wettable surface finish. |
| Impermeable Barrier | 1 mil Polyethylene Film (Grade and Filler content) |
| Bottom Absorbent Material | 125 gsm, 0.08 g/cc airlaid composed of 90 percent Southern Softwood (NB416) and 10 percent 2.8 dpf binder fiber, (T-255) with a wettable surface finish. |

EXAMPLE 14

This is an absorbent article for managing viscoelastic fluids.

| | |
|---|---|
| Cover or Topsheet | 3.5 dpf, 0.6 osy Polypropylene Spunbond (92 percent Union Carbide E5D47 PP + 8 percent AMPACET ® 41438 TiO$_2$ (50 percent concentrate) and point bonded using Hansen & Pennings (HP) pattern. Web was topically treated to 0.3 percent AHCOVEL ® Base N62 (ICI Surfactants, Delaware). |
| Pink Cue | 2.8 dpf, 0.8 osy polypropylene spunbond treated with 0.3 percent AHCOVEL ® Base N62 (ICI Surfactants, Wilmington, Delaware) |
| Upper Absorbent Material | 94 gsm, 0.07 g/cc airlaid 40 percent 6 dpf, Polyester T-224, 40 percent Southern Softwood (NB416), 20 percent 2.8 dpf binder fiber (T-255) with a wettable surface finish. |
| Absorbent Material Pledget | E-folded pledget 204 gsm (note that this is 612 gsm applying our definition of Composite And assuming that e-folded implies that there are three layers of same material composition), 0.11 g/cc airlaid composed of 90 percent Southern Softwood (NB416) and 10 percent 2.8 dpf binder fiber, (T-255) with a wettable surface finish. |
| Impermeable Barrier | 1 mil Polyethyene Film (Grade and Filler Content) |

EXAMPLE 15

This is an absorbent article for managing viscoelastics fluids.

| | |
|---|---|
| Cover or Topsheet | 3.5 dpf, 0.6 osy Polypropylene Spunbond (92 percent Union Carbide E5D47 PP + 8 percent AMPACET ® 41438 TiO$_2$ (50 percent concentrate) and point bonded using Hansen & Pennings (HP) pattern. Web was topically treated to 0.3 AHCOVEL ® Base N62 (ICI Surfactants, Delaware). |
| Pink Cue | 2.8 dpf, 0.8 osy polypropylene spunbond treated with 0.3 percent AHCOVEL ® Base N62 (ICI Surfactants, Wilmington, Delaware) |
| Upper Absorbent Material | 106 gsm, 0.08 g/cc airlaid 40 percent 6 dpf, Polyester T-224, 40 percent Southern Softwood (NB416), 20 percent 2.8 dpf binder fiber (T-255) with a wettable surface finish. |
| Absorbent Material Pledget | E-folded pledget 210 gsm (note that this is 612 gsm applying our definition of Composite And assuming that e-folded implies that there are three layers of same material composition), 0.13 g/cc airlaid composed of 80 percent Southern Softwood (NB416), 10 percent superabsorbent particulate AFA-173-60B and 10 percent 2.8 dpf binder fiber, (T-255) with a wettable surface finish. |
| Impermeable Barrier | 1 mil Polyethylene Film (Grade and Filler Content) |

EXAMPLE 16

This is an absorbent article for managing viscoelastic fluids.

| | |
|---|---|
| Cover or Topsheet | 3.5 dpf, 0.6 osy Polypropylene Spunbond (92 percent Union Carbide E5D47 PP + 8 percent AMPACET ® 41438 TiO$_2$ (50 percent concentrate) and point bonded using Hansen & Pennings (HP) pattern. Web was topically treated to 0.3 AHCOVEL ® Base N62 (ICI Surfactants, Delaware). |
| Pink Cue | 2.8 dpf, 0.8 osy polypropylene spunbond treated with 0.3 percent AHCOVEL ® Base N62 (ICI Surfactants, Wilmington, Delaware) |
| Upper Absorbent Material | 191 gsm, 0.07 g/cc airlaid 40 percent 6 dpf, Polyester T-224, 40 percent Southern Softwood (NB416), 20 percent 2.8 dpf binder fiber (T-255) with a wettable surface finish. |
| Absorbent Material Pledget | E-folded pledget 204 gsm (note that this is 612 gsm applying our definition of Composite And assuming that e-folded implies that there are three layers of same material composition), 0.11 g/cc airlaid composed of 90 percent Southern Softwood (NB416) and 10 percent 2.8 dpf binder fiber, (T-255) with a wettable surface finish. |
| Impermeable Barrier | 1 mil Polyethylene Film (Grade and Filler content) |
| Bottom Absorbent Material | 125 gsm, 0.14 g/cc airlaid composed of 90 percent Southern Softwood (NB416) and 10 percent 2.8 dpf binder fiber, (T-255) with a wettable surface finish. |

Product Examples

Figure 2A:
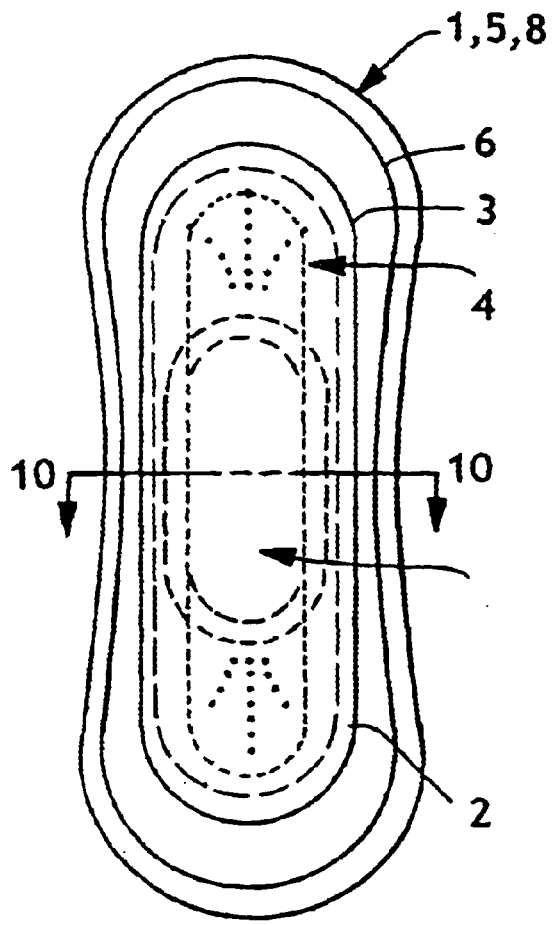
FIG. 2 is another example of a feminine hygiene pad which may contain the absorbent system of the invention.
Figure 2B:
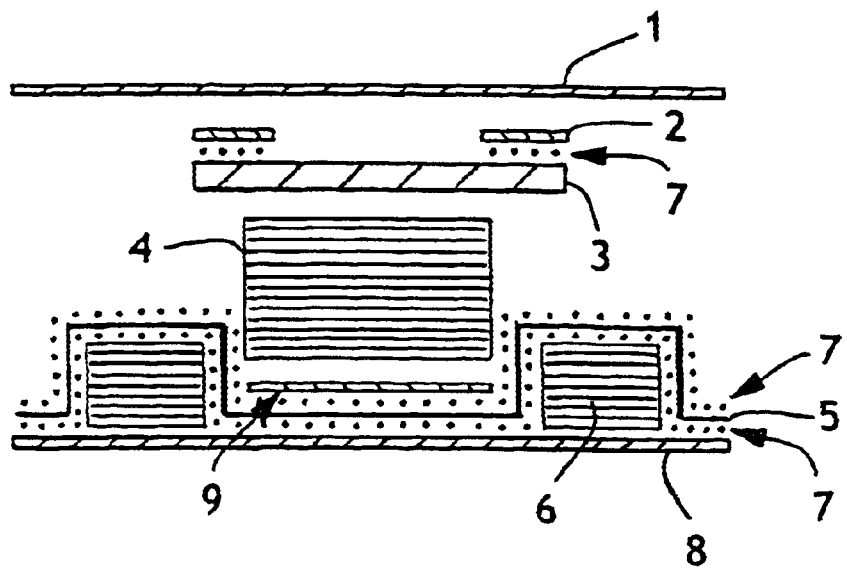

Examples 17–23 refer to FIG. 2.

FIG. 2 contains a plan view (2A) and a cross-sectional view (2B) taken along line 10—10, of an absorbent pad. The absorbent pad has a cover 1, an impermeable barrier 5 and a baffle 8 that are the same size. The pad has a pink cue 2, and an upper absorbent 3 over an absorbent pledget 4. The absorbent pledget 4 is formed onto tissue 9 and is above the impermeable barrier 5. The shaping ring 6 is below the impermeable barrier 5 and above the baffle 8 that protects the wearer's clothing. Construction adhesive 7 in the amount of between 10 and 15 gsm is used to bond the pink cue 2 to the upper absorbent 3 and to bond the barrier 5 to the layers on either side of it. The materials of construction are described in more detail in Examples 17–23.

EXAMPLE 17

This is an absorbent article for managing viscoelastic fluids containing.

Upper Absorbent 104 gsm, 0.11 g/cc airlaid 40 percent 6 dpf, Polyester T-224, 40 percent Southern Softwood (NB416), 20 percent 2.8 dpf binder fiber (T-255) with a wettable surface finish.

| | |
|---|---|
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 18

This is an absorbent article for managing viscoelastic fluids containing.

| | |
|---|---|
| Upper Absorbent | 194 gsm, 0.12 g/cc airlaid 40 percent 6 dpf, Polyester T-224, 40 percent Southern Softwood (NB416), 20 percent 2.8 dpf binder fiber (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 19

This is an absorbent article for managing viscoelastic fluids containing.

| | |
|---|---|
| Upper Absorbent | 109 gsm, 0.075 g/cc airlaid 40 percent 6 dpf, Polyester T-224, 40 percent Southern Softwood (NB416), 20 percent 2.8 dpf binder fiber (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 20

This an absorbent article for managing viscoelastic fluids containing.

| | |
|---|---|
| Upper Absorbent | 203 gsm, 0.07 g/cc airlaid 40 percent 6 dpf, Polyester T-224, 40 percent Southern Softwood (NB416), 20 percent 2.8 dpf binder fiber (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 21

This is an absorbent article for managing viscoelastic fluids containing.

| | |
|---|---|
| Upper Absorbent | 103 gsm, 0.076 g/cc airlaid composed of 90 percent Southern Softwood (NB416) and 10 percent 2.8 dpf binder fiber, (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 22

This is an absorbent article for managing viscoelastic fluids containing

| | |
|---|---|
| Upper Absorbent | 208 gsm, 0.074 g/cc airlaid composed of 90 percent Southern Softwood (NB416) and 10 percent 2.8 dpf binder fiber, (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Poyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 23

This is an absorbent article for managing viscoelastic fluids containing.

| | |
|---|---|
| Upper Absorbent | 119 gsm, 0.06 g/cc airlaid composed of 90 percent Buckeye HPZ3 and 10 percent 2.8 dpf binder fiber, (T-255) with a wettable surface finish. |
| Absorbent Pledget | 636 gsm, 0.11 g/cc fluff (NB416, Weyerhaeuser) - embossed |
| Shaping Ring | 250 gsm, 0.17 g/cc fluff (NB416, unembossed) |
| Impermeable Barrier | 1 mil Polyethylene film, white |
| Pink Cue | 2.8 dpf, 0.8 osy spunbond with 0.3 percent AHCOVEL ® Base N62 (ICI Surfactants, Delaware) |
| Baffle | 1.25 mil polyethylene film, rose colored (Huntsman) |
| Construction Adhesive | National Starch & Chemical (Easymelt 34-5610) |

EXAMPLE 24

An absorbent system consisting of composite A and B that are in liquid communication:
Composite A
  (Option 1—2 inch (5.1 cm)×6 inch 152.4 cm) for FST and 1.5 inch×3 inch (76.2 cm) for TIR)
  150 gsm, 0.08 g/cc airlaid composed of 40% 6 dpf, Polyester T-224, 40% Southern Softwood (NB416), 20% 3.5 dpf copolyester binder fiber (T-254) with a wettable surface finish.
Composite B
  (Option 2—1.5 inch×3 inch (76.2 cm))
  636 gsm, 0.11 g/cc Fluff (Coosa 0054 or NB416)

EXAMPLE 25

An absorbent system consisting of composite A and B that are in liquid communication:
Composite A
  (Option 1—2 inch (5.1 cm)×6 inch (152.4 cm) for FST and 1.5 inch×3 inch (76.2 cm) for TIR)
  150 gsm, 0.08 g/cc airlaid composed of 30% 8 dpf, Trilobal Polyester T-224 with a wettable surface finish, 50% Southern Softwood (NB416), 20% 2.8 dpf binder fiber (T-255) with a wettable surface finish.
Composite B
  (Option 2—1.5 inch×3 inch (76.2 cm))
  636 gsm, 0.11 g/cc Fluff (Coosa 0054 or NB416)

EXAMPLE 26

An absorbent system consisting of composite A and B that are in liquid communication:
Composite A
  (Option 1—2 inch (5.1 cm)×6 inch (152.4 cm) for FST and 1.5 inch×3 inch (76.2 cm) for TIR)
  150 gsm, 0.08 g/cc airlaid composed of 30% 8 dpf, High Void Polyester T-224 with a wettable surface finish, 50% Southern Softwood (NB416), 20% 2.8 dpf binder fiber (T-255) with a wettable surface finish.
Composite B
  (Option 2—1.5 inch×3 inch (76.2 cm))
  636 gsm, 0.11 g/cc Fluff (Coosa 0054 or NB416)

EXAMPLE 27

An absorbent system consisting of composite A and B that are in liquid communication:
Composite A
  (Option 1—2 inch (5.1 cm)×6 inch (152.4 cm) for FST and 1.5 inch×3 inch (76.2 cm) for TIR)
  150 gsm, 0.08 g/cc airlaid composed of 90% Southern Softwood (NB416), 10% 3.5 dpf copolyester binder fiber (T-254) with a wettable surface finish.
Composite B
  (Option 2—1.5 inch×3 inch (76.2 cm))
  636 gsm, 0.11 g/cc Fluff (Coosa 0054 or NB416)

COMPARATIVE SAMPLE 1

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  213 gsm, 0.11 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416

COMPARATIVE SAMPLE 2

Composite A:
  (Option 1—2 inch (5.1 cm)×6 inch (15.2 cm) for FST and 1.5 inch (3.8 cm)×3 inch (7.6 cm) for TIR)
  189 gsm, 0.07 g/cc airlaid 40 percent 6 dpf, Polyester T-224, 40 percent Southern Softwood (NB416), 20 percent 2.8 dpf binder fiber (T-255) with a wettable surface finish.
Composite B:1
  2.8 dpf, 0.08 g/cc, 28 gsm polypropylene spunbond topically treated with 0.3 percent AHCOVEL® (TDL1).
Composite B:2
  (Option 2—1.5 inch (3.8 cm)×3 inch (7.6 cm) for TIR)
  175 gsm, 0.08 g/cc airlaid composed of 90 percent Southern Softwood (NB416) and 10 percent 2.8 dpf binder fiber, (T-255) with a wettable surface finish.

COMPARATIVE SAMPLE 3

Composite A:
  (Option 1—2 inch (5.1 cm)×6 inch (15.2 cm) for FST and 1.5 inch (3.8 cm)×3 inch (7.6 cm) for TIR)
  194 gsm, 0.12 g/cc airlaid composed of 90 percent Southern Softwood (NB416) and 10 percent 2.8 dpf binder fiber, (T-255) with a wettable surface finish.
Composite B:1
  2.8 dpf, 0.08 g/cc, 28 gsm polypropylene spunbond topically treated with 0.3 percent AHCOVEL® (TDL1).
Composite B:2
  (Option 2—1.5 inch (3.8 cm)×3 inch (7.6 cm))
  175 gsm, 0.08 g/cc airlaid composed of 90 percent Southern Softwood (NB416) and 10 percent 2.8 dpf binder fiber, (T-255) with a wettable surface finish.

COMPARATIVE SAMPLE 4

Always© Overnight© Maxi with Wings Universal Product Code (UPCO 37000 30165. Two absorbent core pieces were identified. Upper absorbent was cut to 2 inch (5.1 cm)×6 inch (15.2 cm) for FST and TIR. Bottom absorbent was cut to 2 inch (5.1 cm)×6 inch (15.2 cm) for FST and 1.5 inch (3.8 cm)×3 inch (7.6 cm) for TIR.

COMPARATIVE SAMPLE 5

Kotex© Ultrathin© Maxi UPC 36000 03014. Three absorbent core pieces were identified. Upper absorbent was cut to 2 inch (5.1 cm)×6 inch (15.2 cm) for FST and TIR. Middle and Bottom absorbent were cut to 2 inch (5.1 cm)×6 inch (15.2 cm) for FST and 1.5 inch (3.8 cm)×3 inch (7.6 cm) for TIR.

COMPARATIVE SAMPLE 6

Composite A:
  (Option 1—2 inch (5.1 cm)×6 inch (15.2 cm) for FST and 1.5 inch (3.8 cm)×3 inch (7.6 cm) for TIR)
  206 gsm, 0.06 g/cc airlaid composed of 90 percent Southern Softwood (NB416) and 10 percent 2.8 dpf binder fiber, (T-255) with a wettable surface finish.
Composite B:
  (Option 2—4.5" (11.4 cm)×3 inch (7.6 cm) for FST) 204 gsm, 0.12 g/cc airlaid composed of 90 percent Southern Softwood (NB416) and 10 percent 2.8 dpf binder fiber, (T-255) with a wettable surface finish.

COMPARATIVE SAMPLE 7

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  96.9 gsm, 0.12 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  636 gsm, 0.11 g/cc Fluff (Coosa 0054 or NB416)

COMPARATIVE SAMPLE 8

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  419 gsm, 0.08 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  611 gsm, 0.12 g/cc airlaid composed of 80 percent Southern Softwood (NB416), 10 percent superabsorbent particulate AFA-173-60B and 10 percent 2.8 dpf binder fiber, (T-255) with a wettable surface finish.

COMPARATIVE SAMPLE 9

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  628 gsm, 0.08 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  611 gsm, 0.12 g/cc airlaid composed of 90 percent Southern Softwood (NB416) and 10 percent 2.8 dpf binder fiber, (T-255) with a wettable surface finish.

COMPARATIVE SAMPLE 10

An absorbent system comprising Composite A and B that are in liquid communication.
Composite A:
  (Option 1—2 inch (5.1 cm)×6 inch (15.2 cm) for FST and 1.5 inch (3.8 cm)×3 inch (7.6 cm) for TIR)
  419 gsm, 0.08 g/cc airlaid composed of 90 percent Southern Softwood (NB416) and 10 percent 2.8 dpf binder fiber, (T-255) with a wettable surface finish.
Composite B:
  (Option 2—1.5 inch (3.8 cm)×3 inch (7.6 cm))
  610 gsm, 0.07 g/cc airlaid composed of 90 percent Southern Softwood (NB416) and 10 percent 2.8 dpf binder fiber, (T-255) with a wettable surface finish.

The examples described above pertain to the absorbent systems which define this invention as well as their utilization in absorbent articles. Table 1 lists a number of different material parameters for each of the absorbent system examples; composition, fundamental material characteristics, and test results for the absorbent system examples. Table 2 contains a number of material characteristics that are used in calculating fundamental characteristics. The models used for these calculations are described in depth in "test methods" above. Looking at Table 1 one notes that the example number is referenced to a Composite A formulation (Upper Layer Description) and a Composite B formulation (Lower Layer prescription). Likewise, Table 2 also refers to the Upper Layer (Composite A) and Lower Layer (Composite B). After these formulations Table 1 lists the average density and average basis weight for each of the composites that were tested in these experiments. In Table 2, the capillary tension, permeability, and void volume are calculated for each material. A value of CTB-CTA is also reported and is known as the capillary tension difference or differential and is the capillary tension of Composite B minus the capillary tension of Composite A. In the last three columns, fluid handling data via Bench Test Results is communicated. The first value, "% Fluid in Layer A" is the partitioning amount of fluid in Composite A measured with the Flat System Test. IT3 is the third triple intake time in seconds, measured with the triple intake rewet test. Rewet is the rewet value reported in grams as measured with the triple intake rewet test.

Most absorbent articles for feminine care attempt to distribute menses across the length of the product while keeping the fluid in the center. Unfortunately, due to its viscoelastic nature, menses is difficult to wick both in terms of volume, distance and time compared to Newtonian fluids such as urine. One is also left with the undesirable effect of having large amounts of fluid next or near the body causing the pad to increase in stiffness compared to the dry pad thus reducing conformability. One also tends to decrease comfort by increasing wetness. Therefore one embodiment of this invention is to provide an absorbent systems such that there is an open resilient composite (Composite A) near the liner or topsheet which can be desorbed and which retains very little fluid. To achieve this phenomenon the characteristics of the absorbent beneath the structure must be complementary. This function is measured using the flat systems test by determining the amount of fluid in Composite A. One could envision that materials would tend to transfer for Composite A structures that have low capillary tension, high permeability, and low to intermediate void volume assuming that the capillary tension differential CTB-CTA is greater than 1. We observe this phenomenon by comparing examples 1–6 to Comparative Sample (CS) 1 and CS7 where we note that more fluid tends to remain in Composite A for Composite A structures with higher capillarity and lower permeability. If one compares CS8 and CS10, one notes that as the capillary tension ratio decreases from 1.7 to 0.5, the amount of fluid in Composite A increases from 29 to 89. This is also observed by comparing examples CS2 and CS3.

Geometry of the sample has an impact on fluid partitioning. Stated another way, material characteristics are important but enough of the proper material in the proper orientation is necessary for superior fluid transfer. For instance, comparing Examples 11 and 23, one notes that as porosity (epsilon) multiplied by thickness decreases from 0.51 to 1.50, the fluid partitioning in Composite A increases from 19 to 32 percent. Comparing Examples 3, 9 and 10, one observes that fluid partitioning is similar for materials of different composition but similar fundamental characteristics. Superabsorbent containing structures, however, can be challenging for designing for managing menses. In this case, the capillary tension ratio is large for the materials, however, for materials with smaller capillary tension ratios, superabsorbent containing structures may demonstrate differences in fluid transfer compared to those which do not contain superabsorbent even though initial fundamental parameters are similar. This effect is believed to be due to the swelling of the superabsorbent which increases the pore size of the composite thus decreasing capillarity and the capillary tension ratio of the absorbent system throughout its use, possibly creating a negative capillary tension differential.

Intake time is a measure of the absorbency of a product. One would anticipate that Composite A structures with low capillary, low permeability and high void volume and absorbent systems with high capillarity ratios would have low third intake times. One notes that this trend is true in comparing Examples 1–5 to CS1 and CS7, we observe that intake time decreases with increase in Composite A permeability or decrease in capillarity. Comparing example 6 and 7, one observes that the two structures have similar rewets although code 7 has much lower void volume. This decrease in rewet may be due to an increase in resiliency provided by the HPZ3 fiber compared to the NB416 fiber. CS3, CS4, and CS5 all have high intake times. In the case of CS5 it is believed to be due to low capillarity ratio and in the case of CS3 and CS4 it is believed to be due to small value of porosity multiplied by thickness.

Rewet value is another important parameter since it is a measure of the ability of an absorbent systems to retain fluid under uniaxial compression. It is thus a function of the resiliency of the structure as well as the material characteristics. One skilled in the art would expect that structures that have good intake and transfer would have low rewet values provided that porosity multiplied by thickness values are sufficiently high and that the capillarity of the lower material is high. Low rewet values may also be provided by high capillarity top layers or composites provided that enough space (void volume) is available for the fluid insults. One observes that for CS3–CS5, rewet values are high because of poor intake presumably due to low porosity multiplied by thickness values, low void volume in Composite A or low capillarity differentials. CS10 has higher rewet than CS8 due to decrease in capillarity differentials. Materials with low rewet values have high capillary tensions or intermediate values of capillary tension with larger void volumes, see Examples 1–5, CS1 and CS7. An ideal absorbent system would ideally have low intake times, low rewet values, and low fluid retention in upper materials.

As will be appreciated by those skilled in the art, changes and variations to the invention are considered to be within the ability of those skilled in the art. Such changes and variations are intended by the inventors to be within the scope of the invention.

TABLE 1

System Composition Description

| | Upper Layer Description | | | | | | Lower Layer Description | | | |
| | Fiber Composition | | | Basis | | Is TDL | Fiber Composition | | | |
| Example | % Pulp | % Binder | % PET | Weight (gsm) | Density (g/cc) | Present ? | % Pulp | % Binder | % PET | % SAP |
|---|---|---|---|---|---|---|---|---|---|---|
| 1 | 40% | 20% | 40% | 104.2 | 0.11 | N | 100 | 0 | 0% | 0% |
| 2 | 40% | 20% | 40% | 194.2 | 0.12 | N | 100 | 0 | 0% | 0% |
| 3 | 40% | 20% | 40% | 108.5 | 0.07 | N | 100 | 0 | 0% | 0% |
| 4 | 40% | 20% | 40% | 203.2 | 0.07 | N | 100 | 0 | 0% | 0% |
| 5 | 90% | 10% | 0% | 103.3 | 0.08 | N | 100 | 0 | 0% | 0% |
| 6 | 90% | 10% | 0% | 207.5 | 0.07 | N | 100 | 0 | 0% | 0% |
| 7 | 90% HPZ | 10% | 0% | 118.8 | 0.06 | N | 100 | 0 | 0% | 0% |
| 8 | Bilayer | | | 154 | 0.095 | N | 73% | 13% | 13% | 0% |
| 9 | 40% | 20% | 40% | 94.3 | 0.07 | N | 90% | 10% | 0% | 0% |
| 10 | 40% | 20% | 40% | 106.3 | 0.08 | N | 80% | 10% | 0% | 10% 60B |
| 11 | 90% | 10% | 0% | 190.7 | 0.07 | N | 90% | 10% | 0% | 0% |
| 12 | 90% | 10% | 0% | 182.1 | 0.07 | N | 90% | 10% | 0% | 0% |
| CS1 | 90% | 10% | 0% | 212.3 | 0.11 | N | 100 | 0 | 0% | 0% |
| CS2 | 40% | 20% | 40% | 189.0 | 0.07 | Y | 90% | 10% | 0% | 0% |
| CS3 | 90% | 10% | 0% | 194.2 | 0.12 | Y | 90% | 10% | 0% | 0% |
| CS4 | Always ® brand Ultrathin Feminine Pad | | | | | | | | | |
| CS5 | Kotex ® brand Ultrathin Feminine Pad | | | | | | | | | |
| CS6 | 90% | 10% | 0% | 205.8 | 0.06 | N | 90% | 10% | 0% | 0% |
| CS7 | 90% | 10% | 0% | 96.9 | 0.12 | N | 100 | 0 | 0% | 0% |
| CS8 | 90% | 10% | 0% | 418.5 | 0.08 | N | 90% | 10% | 0% | 0% |

TABLE 1-continued

System Composition Description

| | Upper Layer Description | | | | | Is TDL | Lower Layer Description | | | |
|---|---|---|---|---|---|---|---|---|---|---|
| | Fiber Composition | | | Basis | | Present | Fiber Composition | | | |
| Example | % Pulp | % Binder | % PET | Weight (gsm) | Density (g/cc) | ? | % Pulp | % Binder | % PET | % SAP |
| CS9 | 90% | 10% | 0% | 627.8 | 0.08 | N | 90% | 10% | 0% | 0% |
| CS10 | 90% | 10% | 0% | 418.5 | 0.08 | N | 40% | 20% | 40% | 0% |

Bilayer properties were calculated as bulk averages

TABLE 2

Fundamental Properties of Layers in Patent Examples

| | Upper Layer Fluid Handling Fundamentals | | | Lower Layer Fluid Handling Fundamentals | | | Cap. Tension Gradient $CT_B - CT_A$ (cm saline) | Bench Test Results | | |
|---|---|---|---|---|---|---|---|---|---|---|
| Ex. | Cap. Tension ($CT_A$) (cm saline) | Kozeny-Carmen Perm. (Darcy) | Void Volume ($VV_A$) (cc/cm$^2$) | Cap. Tension ($CT_B$) (cm saline) | Kozeny-Carmen Perm. (Darcy) | Void Volume ($VV_B$) (cc/cm$^2$) | | % Fluid in Layer A | 3rd Intake Time (sec) | Rewet (g) |
| 1 | 8.7 | 253 | 0.09 | 15.8 | 163 | 0.53 | 7.1 | 8% | 40 | 0.17 |
| 2 | 10.0 | 205 | 0.14 | 15.8 | 163 | 0.53 | 5.8 | 13% | 23 | 0.16 |
| 3 | 5.8 | 459 | 0.14 | 15.8 | 163 | 0.53 | 10.0 | 6% | 17 | 0.17 |
| 4 | 5.1 | 541 | 0.29 | 15.8 | 163 | 0.53 | 10.7 | 11% | 25 | 0.19 |
| 5 | 9.7 | 300 | 0.13 | 15.8 | 163 | 0.53 | 6.1 | 10% | 32 | 0.20 |
| 6 | 9.4 | 312 | 0.27 | 15.8 | 163 | 0.53 | 6.4 | 20% | 29 | 0.06 |
| 7 | 6.0 | 453 | 0.20 | 15.8 | 163 | 0.53 | 9.8 | 20% | 24 | 0.06 |
| 8 | 10.7 | 241 | 0.151 | 16.4 | 142 | 0.45 | 5.7 | 16% | 29 | 0.18 |
| 9 | 5.7 | 472 | 0.12 | 16.4 | 142 | 0.45 | 10.7 | 8% | 35 | 0.10 |
| 10 | 5.8 | 440 | 0.13 | 15.8 | 154 | 1.30 | 10.0 | 8% | 28 | 0.26 |
| 11 | 9.0 | 356 | 0.27 | 16.4 | 142 | 0.45 | 7.4 | 19% | 30 | 0.08 |
| 12 | 8.3 | 375 | 0.27 | 16.4 | 142 | 0.45 | 8.1 | 18% | 30 | 0.03 |
| CS1 | 14.2 | 175 | 0.18 | 15.8 | 163 | 0.53 | 1.6 | 25% | 51 | 0.11 |
| CS2 | 5.8 | 465 | 0.24 | 10.2 | 277 | 0.21 | 4.4 | 23% | 28 | 0.87 |
| CS3 | 15.2 | 158 | 0.16 | 10.2 | 277 | 0.21 | −5.0 | 78% | 237 | 1.18 |
| CS4 | | | | | | | | 23% | >300 | 1.93 |
| CS5 | | | | | | | | 85% | >300 | 1.02 |
| CS6 | 7.6 | 423 | 0.33 | 16.4 | 142 | 0.15 | 8.8 | 32% | 39 | 0.77 |
| CS7 | 15.2 | 159 | 0.08 | 15.8 | 163 | 0.53 | 0.6 | 16% | 52 | 0.09 |
| CS8 | 9.7 | 295 | 0.52 | 16.4 | 142 | 0.45 | 6.7 | 29% | 61 | 0.07 |
| CS9 | 9.7 | 295 | 0.78 | 16.4 | 142 | 0.45 | 6.7 | 49% | | |
| CS10 | 9.7 | 295 | 0.52 | 5.1 | 541 | 0.87 | −4.6 | 89% | 55 | 0.33 |

Bilayer properties were calculated as bulk averages

What is claimed is:

1. An absorbent article comprising:

a liquid impermeable backsheet, and;

a liquid permeable topsheet, and;

an absorbent system located between said topsheet and said backsheet, comprising a first absorbent composite which has a first permeability, a first capillary tension, a first porosity, a first thickness and a first void volume and at least one second absorbent composite which has a second capillary tension, a second porosity and a second thickness, wherein said first absorbent composite is in liquid communication with said second absorbent composite, such that said first absorbent composite and said second absorbent composite have a fluid partitioning amount in said first composite of less than about 22 percent, a third triple intake time as determined using a triple intake rewet test procedure, of less than 40 seconds and a rewet value of less than 0.28 grams.

2. The absorbent article of claim 1 wherein said first absorbent composite has a capillary tension which is less than 7.8 cm saline.

3. The absorbent article of claim 2 wherein said first absorbent composite has a void volume between 0.09 and 0.51 cc/cm$^2$.

4. The absorbent article of claim 3 wherein said first absorbent composite has a permeability greater than 150 darcies.

5. The absorbent article of claim 1 wherein said second absorbent composite has a porosity multiplied by thickness greater than 2.1, and wherein a difference in capillary tension between said second and first composites is greater than 1 cm saline.

6. The absorbent article of claim 5 wherein said second absorbent composite has a void volume greater than 0.021 cc/cm$^2$.

7. The absorbent article of claim 1 wherein said first absorbent composite has a capillary tension less than 7.8 cm saline, a void volume between 0.1 and 0.5 cc/cm$^2$, and a permeability between 250 and 500 darcies.

8. The absorbent article of claim 1 wherein said first absorbent composite has at least two layers.

9. The absorbent article of claim 8 wherein at least one of said first absorbent composite layers is made according to an airlaying process.

* * * * *